United States Patent
Mannion et al.

(10) Patent No.: US 12,232,770 B2
(45) Date of Patent: Feb. 25, 2025

(54) DEFLECTABLE DELIVERY SYSTEM FOR IMPLANT DELIVERY

(71) Applicant: Medtronic, Inc., Minneapolis, MN (US)

(72) Inventors: Madeline A. Mannion, Beverly, MA (US); John B. Horrigan, Beverly, MA (US); Stuart R. MacDonald, Andover, MA (US)

(73) Assignee: Medtronic, Inc., Minneapolis, MN (US)

( * ) Notice: Subject to any disclaimer, the term of this patent is extended or adjusted under 35 U.S.C. 154(b) by 229 days.

(21) Appl. No.: 17/472,251

(22) Filed: Sep. 10, 2021

(65) Prior Publication Data

US 2022/0079624 A1 Mar. 17, 2022

Related U.S. Application Data

(60) Provisional application No. 63/078,626, filed on Sep. 15, 2020.

(51) Int. Cl.
| | |
|---|---|
| *A61B 17/34* | (2006.01) |
| *A61B 17/00* | (2006.01) |
| *A61M 25/00* | (2006.01) |
| *A61M 25/01* | (2006.01) |

(52) U.S. Cl.
CPC .... *A61B 17/3468* (2013.01); *A61B 17/00234* (2013.01); *A61M 25/0009* (2013.01); *A61B 2017/00323* (2013.01); *A61M 2025/015* (2013.01)

(58) Field of Classification Search
CPC .......... A61B 17/3468; A61B 17/00234; A61B 2017/00323; A61M 25/0009; A61M 2025/015; A61N 1/056–059
See application file for complete search history.

(56) References Cited

U.S. PATENT DOCUMENTS

| | | | | |
|---|---|---|---|---|
| 4,846,573 | A | * | 7/1989 | Taylor ................ A61B 1/0055 356/241.4 |
| 5,766,151 | A | * | 6/1998 | Valley ............... A61M 39/0247 604/103.07 |
| 5,960,145 | A | | 9/1999 | Sanchez |
| 6,198,974 | B1 | | 3/2001 | Webster, Jr. |

(Continued)

OTHER PUBLICATIONS

Kirsh, "Enhancing Catheter Steerability and Deflection," medicaldesignandoutsourcing.com, Nov. 7, 2017, 3 pp.

(Continued)

*Primary Examiner* — Shaun L David
*Assistant Examiner* — Rachael L Geiger
(74) *Attorney, Agent, or Firm* — Shumaker & Sieffert, P.A.

(57) ABSTRACT

An example catheter includes an elongate member having a wall defining a longitudinally extending lumen, a fixation member disposed on an exterior surface of the wall of a distal portion of the elongate member, a pull wire extending axially through the wall of the elongate member and coupled to the fixation member, and a member portion encasing at least a portion of the fixation member, where the fixation member is shaped to engage the distal member in response to a pull force applied to the pull wire to cause the elongate member to deflect from an initial configuration to a deflected configuration.

28 Claims, 10 Drawing Sheets

(56) References Cited

U.S. PATENT DOCUMENTS

| | | |
|---|---|---|
| 6,991,616 B2 | 1/2006 | Bencini et al. |
| 7,553,305 B2 | 6/2009 | Honebrink et al. |
| 8,226,641 B2 | 7/2012 | Potter |
| 8,556,893 B2 | 10/2013 | Potter |
| 8,702,647 B2 | 4/2014 | Benscoter et al. |
| 8,734,699 B2 | 5/2014 | Heideman et al. |
| 8,814,824 B2 | 8/2014 | Kauphusman et al. |
| 9,867,964 B2 | 1/2018 | Drake et al. |
| 9,918,859 B2 | 3/2018 | Cummins et al. |
| 9,993,648 B2 | 6/2018 | Kelly et al. |
| 10,188,834 B2 | 1/2019 | Zhang et al. |
| 10,398,543 B1* | 9/2019 | Solar .................... A61F 2/12 |
| 2005/0203604 A1* | 9/2005 | Brabec ................ A61N 1/0565 |
| | | 607/122 |
| 2005/0209564 A1* | 9/2005 | Bonner ............. A61B 17/3478 |
| | | 604/173 |
| 2005/0288613 A1* | 12/2005 | Heil ................. A61B 17/00234 |
| | | 607/129 |
| 2006/0079949 A1* | 4/2006 | Brostrom ............... A61N 1/057 |
| | | 607/119 |
| 2007/0112361 A1* | 5/2007 | Schonholz ....... A61B 17/00234 |
| | | 606/151 |
| 2007/0282358 A1 | 12/2007 | Remiszewski et al. |
| 2008/0091169 A1 | 4/2008 | Heideman et al. |
| 2008/0188800 A1* | 8/2008 | Bencini ............. A61M 25/0144 |
| | | 604/95.04 |
| 2012/0108938 A1 | 5/2012 | Kauphusman et al. |
| 2012/0130192 A1* | 5/2012 | Rasmussen ............. A61F 2/962 |
| | | 600/208 |
| 2015/0051615 A1* | 2/2015 | Schmidt ............... A61N 1/3756 |
| | | 606/129 |
| 2015/0343198 A1* | 12/2015 | Nageri ................. A61N 1/0558 |
| | | 607/116 |
| 2017/0100582 A1* | 4/2017 | McEvoy .............. A61N 1/0573 |
| 2017/0266410 A1* | 9/2017 | Farrell .............. A61M 25/0026 |
| 2019/0008639 A1 | 1/2019 | Landon et al. |
| 2019/0038906 A1* | 2/2019 | Koop ............... A61N 1/37205 |
| 2021/0016056 A1* | 1/2021 | Drake ................ A61M 25/005 |

OTHER PUBLICATIONS

International Search Report and Written Opinion of International Application No. PCT/US2021/050099, dated Feb. 1, 2022, 15 pp.

* cited by examiner

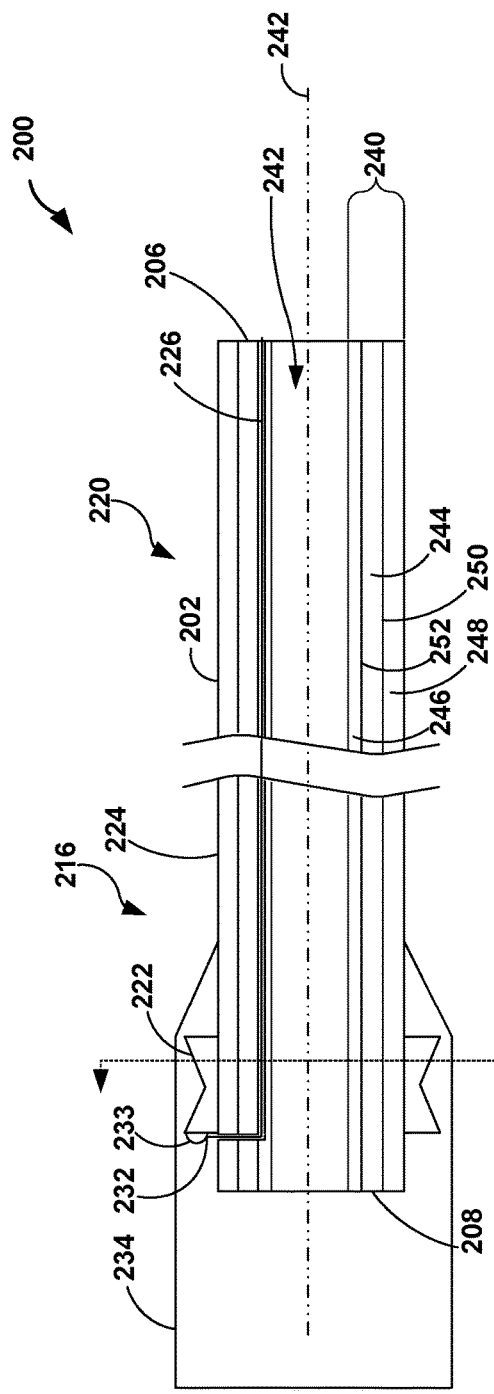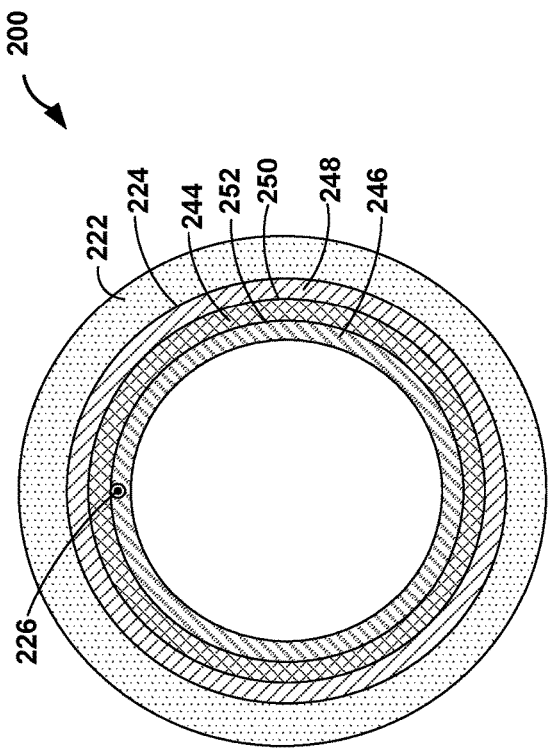
FIG. 2A
FIG. 2B

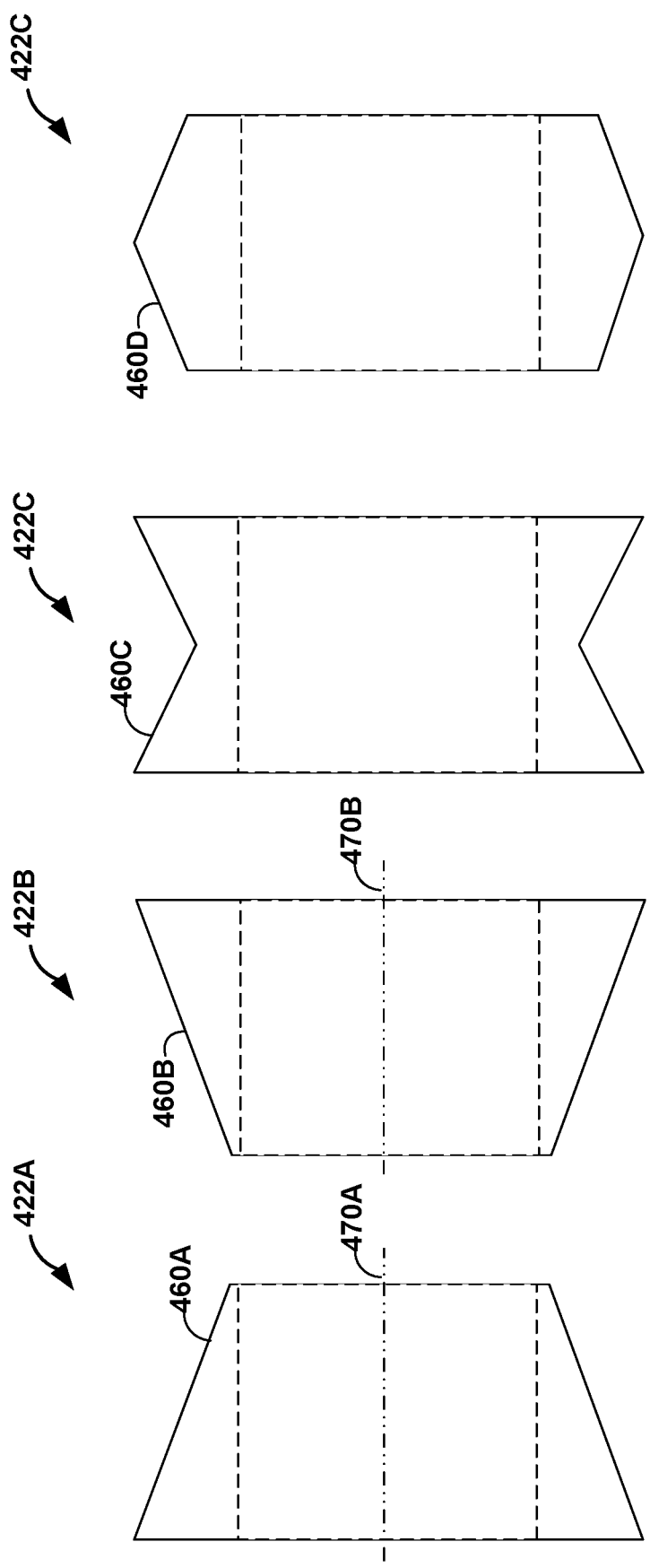

DEFLECTABLE DELIVERY SYSTEM FOR IMPLANT DELIVERY

This application claims the benefit of U.S. Provisional Application No. 63/078,626, filed Sep. 15, 2020, the entire content of which is incorporated herein by reference.

TECHNICAL FIELD

This disclosure relates to medical systems and techniques including deflectable shaft catheters.

BACKGROUND

Interventional medicine techniques may use deflectable shaft catheters to deliver medical therapy and/or provide medical monitoring. Typically, a deflectable shaft catheter includes a pull wire extending along a length thereof, where a distal end of the pull wire is anchored distal to a deflectable segment of the shaft. A proximal end of the pull wire is typically secured to a control member subassembly mounted in a handle of the catheter.

SUMMARY

The present disclosure describes example medical systems including deflectable catheters and techniques including the use and manufacture of deflectable catheters. The described deflectable catheters include an overmolded distal end and a pull wire or cord anchored to a fixation member. The fixation member may be coupled to an elongate member of the catheter by the overmolded distal end. Coupling the fixation member to the elongate member using the overmolded distal end may reduce manufacturing cost and/or complexity relative to catheters that include pull rings embedded in the elongate member. Additionally or alternatively, the fixation member may improve transfer of a pull force (e.g., in the proximal direction relative to the elongate member) and/or a push force (e.g., in the distal direction relative to the elongate member) from the pull wire to the distal end of the catheter and/or reduce decoupling of the pull wire from the distal end of the elongate member compared to pull wires that are anchored to the elongate member without the described fixation members.

In some examples, a catheter may include an elongate member, a fixation member, a pull wire, and a distal member. The elongate member extends from a proximal end to a distal end, and includes a wall defining a longitudinally extending lumen. The fixation member is disposed on an exterior surface of the wall of a distal portion of the elongate member. The pull wire extends axially through the wall of the elongate member from the proximal end of the elongate member to the fixation member and is coupled to the fixation member. The distal member extends from the distal portion of the elongate member to a distal end of the distal member and encases at least a portion of the fixation member. The fixation member is shaped to engage the distal member. The elongate member is configured to deflect from an initial configuration to a deflected configuration in response to a pull force applied to the pull wire.

In some examples, a method may include forming an elongate member extending from a proximal end to a distal end, the elongate member including a wall defining a longitudinally extending lumen. The method also includes positioning a fixation member on an exterior surface of the wall on a distal portion of the elongate member. The method also includes anchoring a pull wire to the fixation member, where the pull wire extends through the wall of the elongate member from the proximal end of the elongate member to the fixation member. The method also includes forming a distal member over at least a portion of the fixation member and a portion of the distal portion of the elongate member, the distal member extending from the distal portion of the elongate member to a distal end of the distal member and encasing at least a portion of the fixation member. The fixation member is shaped to engage the distal member. The elongate member is configured to deflect from an initial configuration to a deflected configuration in response to a pull force applied to the pull wire.

The details of one or more examples are set forth in the accompanying drawings and the description below. Other features, objects, and advantages will be apparent from the description and drawings, and from the claims.

BRIEF DESCRIPTION OF THE DRAWINGS

FIGS. 2A and 2B are conceptual diagrams illustrating lateral and axial cross-sectional views of an example catheter.

FIGS. 4A-4D are conceptual diagrams illustrating lateral cross-sectional views of respective example fixation members.

DETAILED DESCRIPTION

The disclosure describes example medical systems including deflectable catheters and techniques including the use and manufacture of deflectable catheters. An example deflectable catheter includes an elongate member and a deflection assembly. The deflection assembly includes a handle, an elongate pull wire, and a control member. The elongate member includes a wall extending from a proximal end to a distal end and defining a longitudinally extending lumen. The proximal end of the elongate member may be coupled to a handle of the deflection assembly. The elongate pull wire of the deflection assembly extends from a fixation member at a distal portion of the elongate member to the control member, e.g., through at least a portion of the wall of the elongate member.

The fixation member is configured to reduce manufacturing cost and/or complexity, improve transfer of a pull force and/or a push force from the pull wire to the distal end of the catheter, and/or reduce decoupling of the pull wire from the distal end of the elongate member, e.g., in response to a push force and/or pull force. The fixation member may define any suitable shape to transfer the force from the pull wire to the elongate member and reduce decoupling of the pull wire from the distal end of the elongate member. In some examples, the shape of the fixation member is selected to transfer the force substantially evenly about a circumference of the elongate member, for example, without deforming the lumen of the catheter.

The fixation member may be integrally formed with the pull wire or separately formed and mechanically fixed to the pull wire. In examples in which the pull wire is integrally formed with the fixation member, a distal segment of the pull wire may define at least a portion of the fixation member. For example, the portion of the fixation member may include a winding of the pull wire circumscribing an exterior surface of the elongate member of the catheter. In examples in which the fixation member is separately formed, the fixation member may define an annulus configured to receive the elongate member of the catheter therein. The pull wire may be anchored to the fixation member by welding, adhesive, or mechanical fixation.

Figure 1:
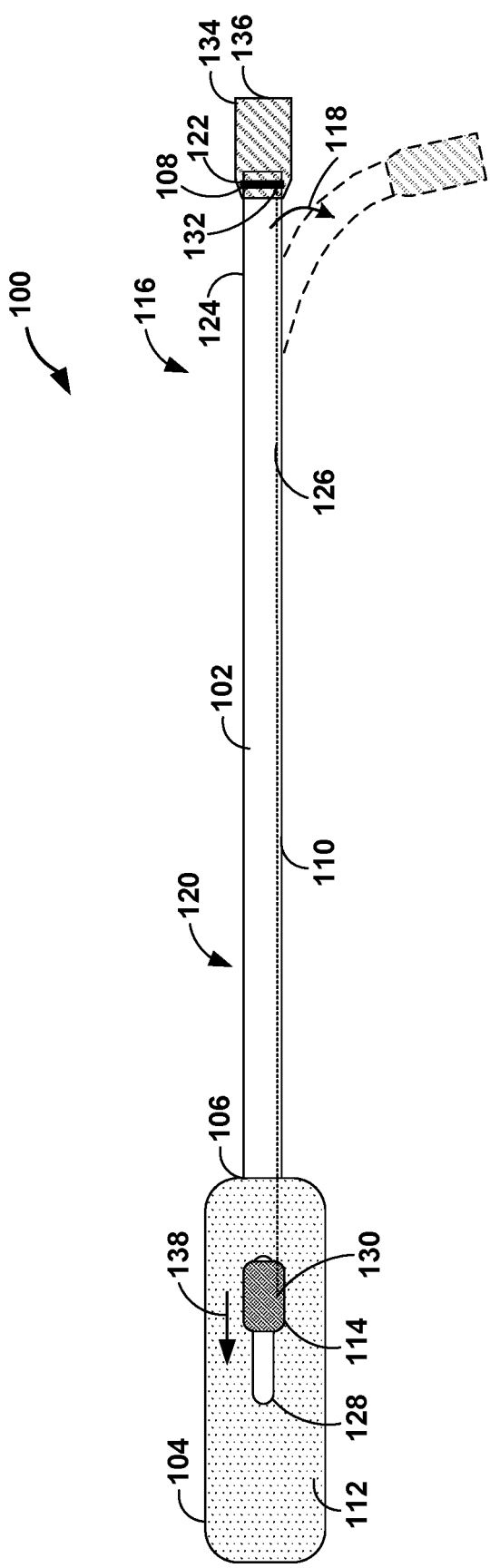
FIG. 1 is a conceptual diagram illustrating a plan view of an example deflectable catheter.

FIG. 1 is conceptual diagram illustrating a plan view of an example deflectable catheter 100. Deflectable catheter 100 including an elongate member 102 and a deflection assembly 104. Elongate member 102 extends from a proximal end 106 to a distal end 108. Elongate member 102 includes a wall 110 defining a longitudinally extending lumen (not shown).

Wall 110 may include one or more material layers. For example, wall 110 may include one or more polymeric material layers. In some examples, wall 110 may include an elongate core layer, an inner layer, and an outer layer. The elongate core layer may include a substantially resilient material, e.g., relative to the inner layer and/or outer layer. In some examples, elongate core layer may include a coiled wire, braided metal wire, or laser cut metal hypotube, such as, for example, stainless steel or nitinol, defining an exterior surface and an interior surface defining the lumen of elongate member 102. The inner layer may include a polymer, such as, for example, polytetrafluoroethylene or other polymer having a low coefficient of friction (e.g., relative to the elongate core layer), disposed on the interior surface of the elongate core layer. The outer layer may include a polymer, such as, for example, polyether block amide or other flexible polymers, disposed on the exterior surface of the elongate core layer.

Proximal portion 120 (e.g., proximal end 106) of elongate member 102 is coupled to deflection assembly 104. Deflection assembly 104 includes a hub assembly (not shown), a handle 112, a control member 114, and a pull wire 126. The hub assembly may be coupled to at least a portion of proximal portion 120 (e.g., proximal end 106) of elongate member 102 and configured to enable a push force to be applied to pull wire 126. For example, hub assembly may surround pull wire 126 in sliding engagement to constrain pull wire in response to a push force. Handle 112 may be configured to surround and engage at least a portion of the hub assembly. Additionally, or alternatively, at least a portion of proximal portion 120 (e.g., proximal end 106) of elongate member 102 may be coupled directly to handle 112. Control member 114 may be slidably engaged with handle 112. For example, handle 112 may define track 128, along which control member 114 may move (e.g., in the proximal-distal direction).

Pull wire 126 extends from a proximal end 130 to a distal end 132. Proximal end 130 of pull wire 126 may be coupled to control member 114. In some examples, deflection assembly 104 may include a hypotube (not shown) extending from a distal end of the hypotube directly coupled to proximal end 130 of pull wire 126 to a proximal end of the hypotube directly coupled to control member 114. Pull wire 126 may extend through, for example, at least a portion of the hub assembly, handle 112, and/or wall 110 of elongate member 102. For example, handle 112 may be configured to surround at least a portion of pull wire 126 and/or the hypotube extending from the hub assembly to control member 114. Pull wire 126 may include any suitable inextensible and/or incompressible material. In some examples, pull wire 126 may include a metal, such as, stainless steel or nitinol, formed into an elongate wire, coil, or braid.

Distal end 132 of pull wire 126 may be coupled (e.g., anchored) to a fixation member 122. For example, pull wire 126 may be adhered, welded, or fastened to fixation member 122 and/or define at least a portion of fixation member 122. Fixation member 122 may be coupled to an exterior surface 124 of wall 110 on distal portion 116 of elongate member 102. For example, distal portion 116 of catheter 100 includes a distal member 134. Distal member 134 may extend from a portion of elongate member proximal to fixation member 122 to distal end 136. In this way, distal member 134 may encase at least a portion of fixation member 122 to fix and/or couple fixation member 122 to distal portion 116 of elongate member 102. In some examples, distal member 134 may be overmolded on to distal portion 116 to encase fixation member 122. Additionally or alternatively, fixation member 122 may be coupled to exterior surface 124 and/or distal member 134 by one or more of an adhesive, a friction fit, a thermal weld, one or more fasteners, or the like.

In some examples, fixation member 122 may include any suitable shape defining an aperture that is configured to receive distal portion 116 of elongate member 102 therethrough. For example, fixation member 122 may define an annular shape configured to transfer the force from pull wire 126 to distal portion 116 of elongate member 102 and/or reduce decoupling of pull wire 126 from distal portion 116 of elongate member 102. In some examples, the shape of fixation member 122 is selected to transfer the force substantially evenly about a circumference of elongate member 102, for example, without deforming a lumen of elongate member 102.

In some examples, fixation member 122 may include an annular band. The annular band may define a shape configured to engage distal member 134. For example, the annular band define at least one of a radially outward extending exterior surface, a radially inward extending exterior surface, a taper in a proximal direction, a taper in a distal direction, a taper in both the proximal direction and the distal direction (e.g., a convex shape or a concave shape), a plurality of tapered portions, and/or a textured radially exterior surface. Regardless of the shape, the radially outer surface, e.g., extending in the axial direction, may be substantially rectilinear or curvilinear, within manufacturing tolerances of catheter components. Additionally or alternatively, fixation member 122 may define one or more through-holes (e.g., apertures) extending through fixation member 122 in the radial direction.

In some examples, pull wire 126 and fixation member 122 may be integrally formed. For example, fixation member 122 may include a plurality of coil turns defined by a distal portion of pull wire 126. The plurality of coil turns may extend circumferentially around wall 110 of elongate member 102. The plurality of coil turns may define any suitable shape. In some examples, the plurality of coil turns may define at least one of a convex shape or a concave shape. In some examples, the plurality of coil turns define at least one gap between at least a first coil turn and a second coil turn of the plurality of coil turns. The shape of the plurality of coil turns and/or gaps between adjacent coil turns may be configured to improve engagement of fixation member 122 with distal member 134.

Fixation member 122 may include any suitable material. In some examples, fixation member 122 may include a metal, a biocompatible metal (e.g., suitable for implant or use within the human body), a stainless steel alloy, a nickel titanium alloy, a polymer, a biocompatible polymer, a thermoplastic, polyether ether ketone, or combinations thereof.

Distal member 134 may include any suitable material, such as one or more polymers. At least one of a tensile strength of the one or more polymers of distal member 134 may be greater than a tensile strength of a material of elongate member 102 or a durometer of the one or more polymers of distal member 134 may be greater than a durometer of the material of elongate member 102. In this way, distal member 134 may include a polymer material that is tougher than an outer layer of elongate member 102. The relative toughness of distal member 134 may improve the robustness of pulling and pushing on fixation member 122 via pull wire 126, for example, compared to an attachment of a pull wires directly to elongate member 102 or an anchor band affixed on exterior surface 124 of elongate member 102 or embedded in elongate member 102.

In some examples, distal member 134 may include a portion of the medical balloon, such as a proximal collar of a medical balloon. In some examples, distal member 134 may be configured to receive an implantable medical device (IMD). For example, distal member 134 may be configured to receive an implantable electrical therapy device, such as a cardiac pacing device, a stent, a stented heart valve, endovascular graft, or a drub eluting therapy device. In some examples, distal member 134 may be configured to deploy the IMD. For example, a clinician may introduce distal portion 116 of elongate member 202 into vasculature of a patient. The clinician may guide distal member 134 to a target site within the vasculature of a patient. The target site may include, for example, a target pacing site. Once positioned at the target site, the clinician may deploy the IMD from distal end 136 of distal member 134. For example, deflectable catheter 100 may include any suitable deployment member configured to deploy the IMD from distal end 136 of distal member 134. In some examples, the deployment member may include a control wire having a proximal end coupled to a control member at deflection assembly 104, a medial portion extending through elongate member 102, and a distal end configured to push IMD out of distal member 134. In some examples, distal member 136 may be configured like cup or other open-ended tubular structure, e.g., as shown in FIG. 1.

At least a portion of a distal portion 116 of elongate member 102 is configured to deflect, e.g., in the direction of arrow 118, from an initial configuration (e.g., shown as solid lines in FIG. 1) to a deflected configuration (e.g., shown as dashed lines in FIG. 1). Proximal portion 120 of elongate member 102 may be configured to not deflect when distal portion 116 is deflected. When a clinician slides control member 114 proximally, as indicated by arrow 138, the distal portion 116 of elongate member 102 may deflect from the initial configuration to the deflected configuration. The deflected configuration may enable a clinician to maneuver a distal portion of the elongate member toward a target site within a body of a patient. In some examples, the initial configuration may include a substantially straight configuration, e.g., a straight or nearly straight configuration of elongate member 102. In some examples, the initial configuration may include a bent configuration, e.g., elongate member 102 may define a curve or bend when in a relaxed state without application of a pull force or push force. A bent initial configuration may be selected to aid in deployment or delivery compared to an unbent initial configuration. In some examples, the deflected configuration may include any suitable deflection angle relative to the initial configuration. In some examples, the deflected configuration may include a deflection in a single plane or in two planes.

In some examples, the deflection occurs on the distal portion of elongate member 102 because wall 110 of elongate member 102 is more flexible or more compressible along distal portion 116 relative to proximal portion 120. Generally, the deflected configuration may include any suitable arc degree and/or radius of curvature. In some examples, the arc degree of the deflected configuration may be within a range from about 10 degrees to about 180 degrees, such as from about 20 degree to about 90 degrees. In some examples, the deflected configuration may include two or more deflections in the same direction or different directions. The first and second deflections may be at the same or different longitudinal position relative to elongate member 102. For example, the deflected configuration may include a first deflection (e.g., in the plane of the page as illustrated in FIG. 1) and a second deflection in a second direction at the same or a different longitudinal position (e.g., out of the plane of the page as illustrated in FIG. 1).

When the clinician releases control member 114 and/or pushes the control member distally back to a home position, pull wire 126 actively pushes elongate member 102 back to the initial configuration. For example, a perimeter of pull wire 126 may be constrained (e.g., surrounded) from fixation member 122 at distal end 108 of elongate member 102 to control member 114. By constraining pull wire 126, a push force applied to pull wire 126 may be transferred from control member 114 to distal portion 116 of elongate member 102, rather than, an unconstrained pull wire bending or buckling in response to the push force. Transfer of the push force by the constrained pull wire 126 enables active return of elongate member 102 from the deflected configuration to the initial configuration. By enabling active return using a single pull wire, the described deflectable catheters provide enhanced function compared to deflectable catheters without active return. For example, a deflectable catheter without active return, upon release of a control member of when in a deflected configuration, may relax toward the initial configuration due to release of strain or elastic deformation in the elongate member. In some examples, a deflectable catheter without active return may be unable to fully return to an initial configuration, for example, due to plastic deformation of at least a portion of the elongate member. Active return deflectable catheter 100, however, may be controlled to return to the initial configuration, as described above.

FIGS. 2A and 2B are conceptual diagrams illustrating lateral and axial cross-sectional views of an example catheter 200. Catheter 200 may be the same as or substantially similar to deflectable catheter 100 describe above in reference to FIG. 1, except for the differences described herein. For example, although not illustrated in FIG. 2A, catheter 200 may include a handle assembly. Catheter 200 includes elongate member 202, fixation member 222, pull wire 226, and distal member 234. In some examples, fixation member 222 may be configured to enable overmolding of distal member 234 on to distal portion 216 of catheter 200. For example, without fixation member 222, overmolding distal member 234 may compress or deform catheter 200.

Elongate member 202 extends from proximal end 206 to distal end 208. As discussed above, elongate member 202 may be configured to deflect from an initial configuration to a deflected configuration in response to a pull force applied to pull wire 226 (e.g., in the proximal direction). In some examples, elongate member 202 may be configured to actively return from the deflected configuration to the initial configuration in response to a push force applied to pull wire 226 (e.g., in the distal direction). Elongate member includes wall 240 defining a longitudinally extending lumen 242. Wall 240 may include an elongate core layer 244, inner layer 246, and outer layer 248, as discussed above. Elongate core layer 244 defines an exterior surface 250 and an interior surface 252. Interior surface 252 may define longitudinally extending lumen 242. Inner layer 246 may be disposed on interior surface 252 of elongate core layer 244. Outer layer 248 may be disposed on exterior surface 250 of elongate core layer 244. In some examples, pull wire 226 may extend through inner layer 246 from proximal end 206 to distal end 208 of elongate member 202. In some examples, pull wire 226 may extend through a separate dedicated lumen between inner layer 246 and core layer 244. In some examples, pull wire 226 may extend through fixation member 222, such as through an aperture or through-hole defined by fixation member 222.

Fixation member 222 is coupled to an exterior surface 224 of wall 240 on a distal portion 216 of elongate member 202. Fixation member 222 may be configured to engage exterior surface 224 by at least one of a friction fit, a compression fit, or another mechanical fitting, such as by adhesion or overmolding. Fixation member 222 is configured to couple to distal portion 232 of pull wire 226. In some examples, distal portion 232 of pull wire 226 may be welded, e.g., by weld bead 233, to fixation member 222. In some examples, distal portion 232 of pull wire 226 may mechanically fixed to fixation member 222 by, for example, a fastener, a screw, a bolt, a winding of pull wire 226 around a portion of fixation member 222, or the like. Additionally or alternatively, fixation member 222 may include a channel or a protrusion having an aperture configured to receive distal portion 232 of pull wire 226 therethrough. When extended through the channel or aperture, an anchor, such as a bulbous structure (e.g., having a diameter larger than a diameter of pull wire 126), a washer, a loop, or a knot, may be fixed to distal portion 232 of pull wire 226 122 to securely retain distal portion 232 of pull wire 226 to fixation member 222. By coupling distal portion 232 of pull wire 226 to fixation member 222, when a pull force and/or a push force is applied to pull wire 226 (e.g., in the proximal direction or distal direction), distal portion 232 of pull wire 226 may transfer the pull force and/or the push force to fixation member 222 and elongate member 202.

In some examples, distal member 234 may be coupled to fixation member 222 and distal portion 232 of pull wire 226. For example, distal member 234 may be overmolded on to fixation member 222 and distal end of pull wire 226 to mechanically couple fixation member 222 and/or distal portion 232 of pull wire 226 to distal portion 216 of elongate member 202. Distal member 234 may be configured to, when a push force and/or a pull force is applied to pull wire 226 (e.g., in the distal direction), transfer the push force and/or a pull force from distal portion 232 of pull wire 226 to the distal member 234, fixation member 222, and/or elongate member 202. In some examples, distal member 234 may be configured to add rigidity to elongate member 202 compared to catheters without an overmolded distal portion. The added rigidity may enable fixation member 222 to transfer the force substantially evenly about a circumference of elongate member 202 to reduce deformation of lumen 242 compared to a catheter without an overmolded distal portion.

Pull wire 226 may be the same as or substantially similar to pull wire 126 discussed above in reference to FIG. 1. For example, pull wire 226 extends through wall 240 of elongate member 202 from proximal end 206 of elongate member 202 to fixation member 222, and pull wire 226 may be coupled to fixation member 222. Pull wire 226 may extend through inner layer 246 or be disposed between inner layer 246 and core layer 244. In some examples, as illustrated in FIG. 2A, pull wire 226 may protrude through outer layer 248 at distal portion 216 of elongate member 202. In other examples, pull wire 226 may protrude through core layer 244 and outer layer 248 to exterior surface 224 of wall 240 at distal portion 216 of elongate member 202 (e.g., at a location distal to fixation member 222. proximal to fixation member 22, or therebetween). In some examples, pull wire 226 may include a sheath or tube surrounding at least a portion of pull wire 226. For example, the sheath or tube may include polytetrafluoroethylene, a polymer having a low coefficient of friction, polyether block amide, or a flexible polymer that is configured to retain pull wire 226 in sliding engagement and resist a lateral force (e.g., against a sidewall of the sheath or tube) from pull wire 226 in response to a pull force and/or a push force applied to pull wire 226.

As discussed above in reference to FIG. 1, a fixation member may include an annular band coupled to a pull wire, the annular band defining a shape configured to engage a distal portion of a catheter. By engaging the distal portion, the fixation member enables transfer of a pull force and/or push force to a distal portion of a catheter and/or reduces decoupling of the pull wire from the distal portion of the catheter. For example, the exterior surface of the fixation member may be shaped to, in response to a push force and/or a pull force, reduce shear at an interface between the fixation member and an overmolded distal portion and/or an interface between the fixation member and the elongate body. In other words, the exterior surface of the fixation member may be shaped to convert at least a portion of the push force and/or the pull force into a compression or tension of at least a portion of the distal portion and/or a distal portion of the elongate member. FIGS. 3-7 are conceptual diagrams illustrating several example fixation members that include an annular band.

Figure 3:
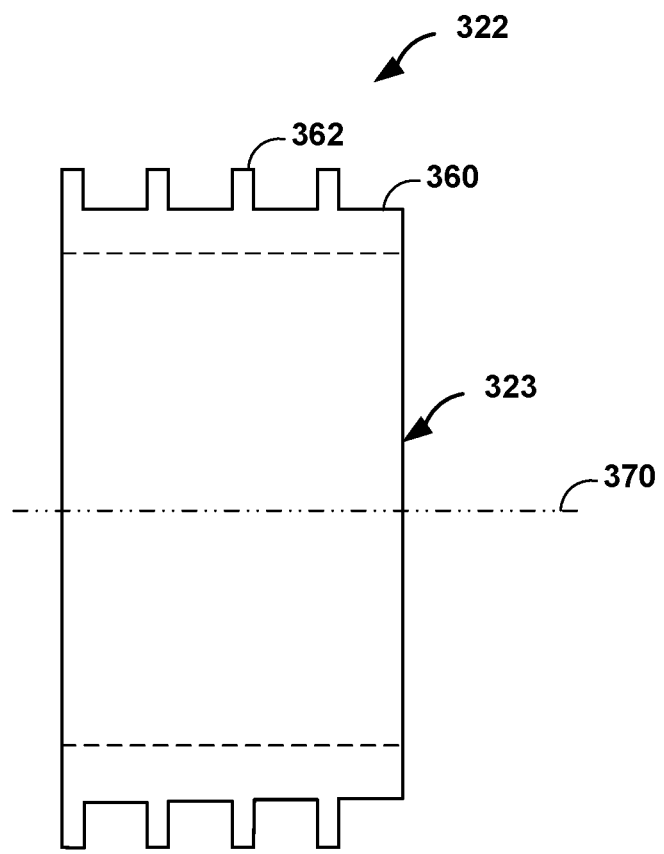
FIG. 3 is a conceptual diagram illustrating a lateral cross-sectional view of an example fixation member.

FIG. 3 is a conceptual diagram illustrating a lateral cross-sectional view of an example fixation member 322. Fixation member 322 may be the same as or substantially similar to fixation members 122 and/or 222 described above in reference to FIGS. 1-2B, except for the differences described herein. Fixation member 322 includes an annular band defining an aperture 323, illustrated as dashed lines. Aperture 323 is sized to receive at least a distal portion of an elongate member (e.g. elongate member 202). Fixation member 322 includes a radially outward extending exterior surface. For example, exterior surface 360 of fixation member 322 defines a plurality of protrusions, e.g., 362, that extend in a radial direction, e.g., relative to a central axis 370 of fixation member 322. Protrusions 362 may extend circumferentially about at least a portion of fixation member 322, extend axially along a least a portion of fixation member 322, extend at an angle between the circumferential direction and the axial direction (e.g., relative to axis 370), or define discrete areas having any suitable shape, such as, for example, rectilinear or curvilinear pillars. Additionally or alternatively, fixation member 322 may define a radially inward extending exterior surface. For example, rather than protrusions 362, exterior surface 360 may define a plurality of recesses. The recesses may define shapes similar to protrusions 362. In some examples, fixation member 322 may include both protrusions 362 and recesses. In some examples, protrusions 362 (and/or recesses) may be formed by any suitable technique such as machining, etching, and/or additive manufacturing. Protrusions 362 (or recesses) are configured to increase a surface area of exterior surface 360 of fixation member 322 and/or provide a mechanical interlock between fixation member 322 and an overmolded distal member. In this way, fixation member 322 enables transfer of a pull force and/or push force to a distal portion of a catheter and/or reduces decoupling of the pull wire (via fixation member 322) from the distal portion of the catheter relative to an anchor ring without protrusions or recesses.

FIGS. 4A-4D are conceptual diagrams illustrating lateral cross-sectional views of respective example fixation members 422A, 422B, 422C, and 422D (collectively, fixation members 422). Fixation members 422 may be the same as or substantially similar to fixation members 122, 222, and/or 322 described above in reference to FIGS. 1-3, except for the differences described herein. Fixation members 422 include a tapered exterior surface. For example, as illustrated in FIG. 4A, fixation member 422A includes exterior surface 460A that is tapered (e.g., relative to axis 470A) in a proximal direction, e.g., relative to an elongate member (e.g., elongate member 102). As illustrated in FIG. 4B, fixation member 422B includes exterior surface 460B that is tapered (e.g., relative to axis 470B) in a distal direction, e.g., relative to an elongate member. As illustrated in FIG. 4C, fixation member 422C includes exterior surface 460C that is tapered in both the distal direction and proximal direction to define a concave shape. As illustrated in FIG. 4D, fixation member 422D includes exterior surface 460B that is tapered in both the distal direction and proximal direction to define a concave shape.

The direction of the taper, angle of the taper, and or number of a plurality of tapers may be selected to enable fixation member 422 to transfer of a pull force and/or push force to a distal portion of a catheter and/or reduce decoupling of the pull wire (via fixation member 422) from the distal portion of the catheter relative to a pull wire anchor without a tapered exterior surface. For example, the angle of the tapered surface may be selected to reduce shear at an interface between fixation member 422 and an overmolded distal member at exterior surface 460 below a selected threshold. In some examples, the threshold may be less than a shear force required to decouple the overmolded distal member from the fixation member 422. Although illustrated as substantially linear tapers, e.g., within common catheter component manufacturing tolerances, in other examples, the tapers may be curvilinear.

Figure 5B:
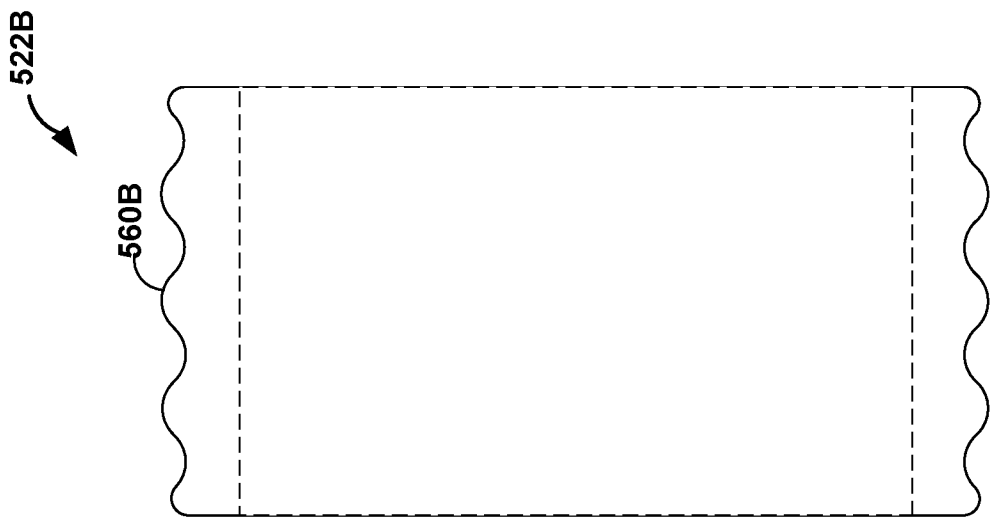
FIGS. 5A and 5B are conceptual diagrams illustrating lateral cross-sectional views of respective example fixation members.
Figure 5A:
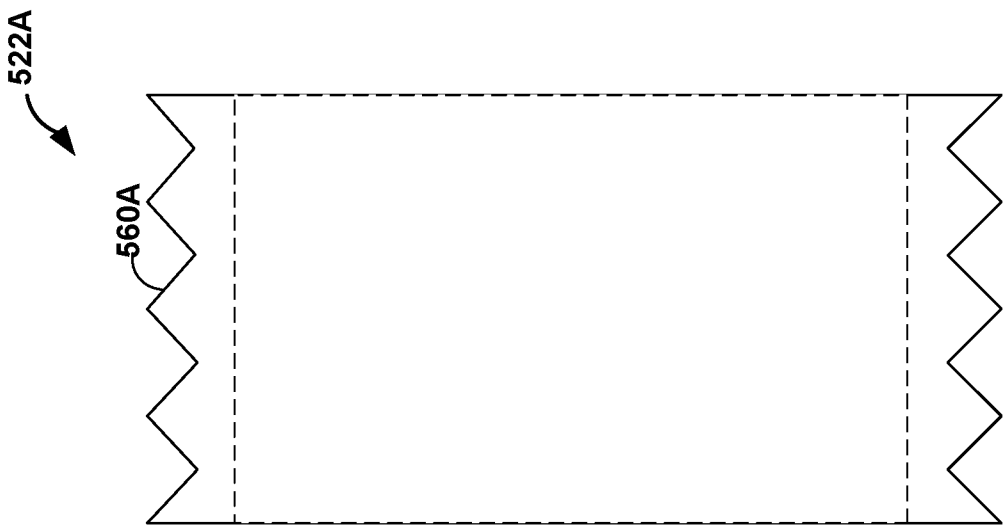

FIGS. 5A and 5B are conceptual diagrams illustrating lateral cross-sectional views of respective example fixation members 522A and 522B (collectively, fixation members 522). Fixation members 522 may be the same as or substantially similar to fixation members 122, 222, 322, and/or 422 described above in reference to FIGS. 1-4D, except for the differences described herein. Fixation members 522 include an exterior surface including a plurality of tapered portions. For example, as illustrated in FIG. 5A, fixation member 422A includes a plurality of rectilinear tapered portions. As illustrated in FIG. 5B, fixation member 422B includes a plurality of curvilinear tapered portions. As discussed above in reference to FIGS. 4A-4D, an angle of the taper, and/or number of a plurality of tapers may be selected to enable fixation members 522 to transfer of a pull force and/or push force to a distal portion of a catheter and/or reduce decoupling of the pull wire (via fixation members 522) from the distal portion of the catheter relative to an anchor ring without a tapered exterior surface.

Figure 6:
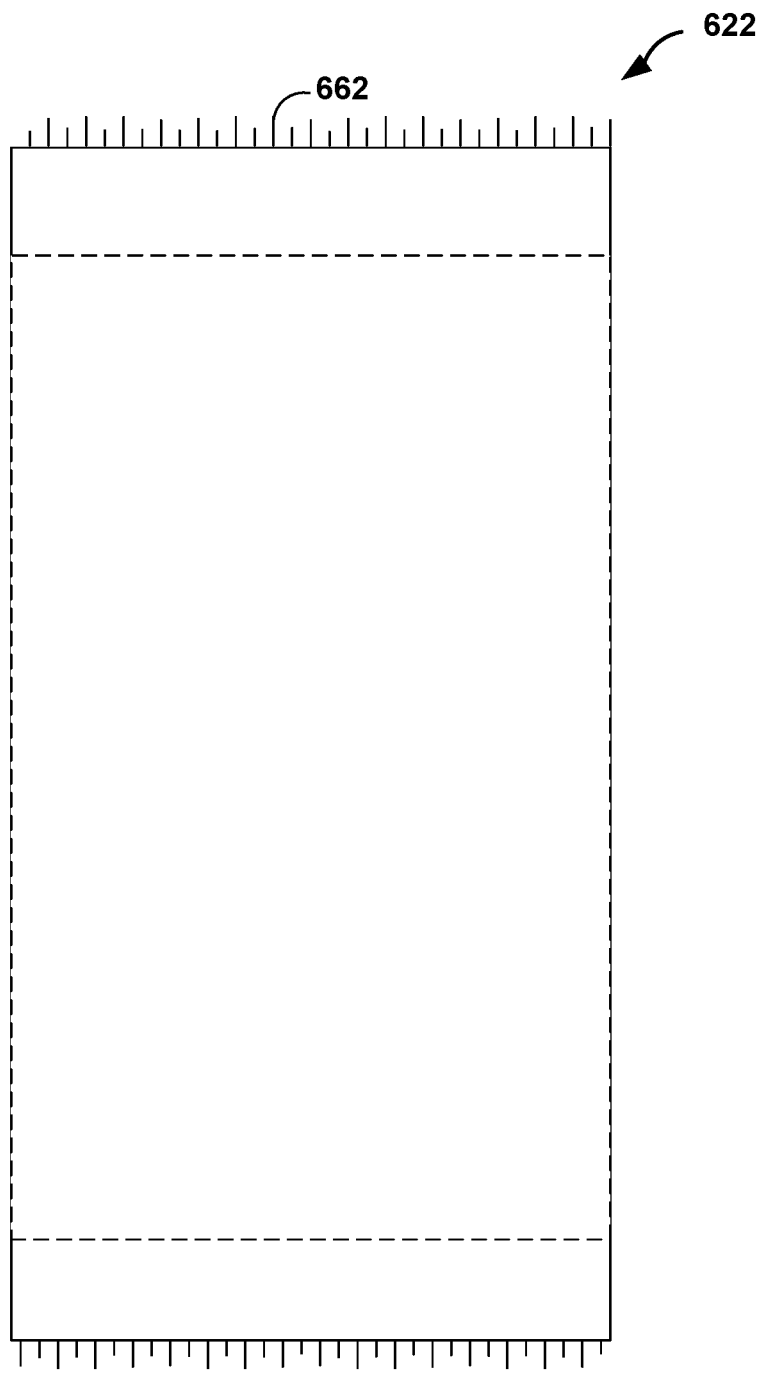
FIG. 6 is a conceptual diagram illustrating a lateral cross-sectional view of an example fixation member.

FIG. 6 is a conceptual diagram illustrating a lateral cross-sectional view of an example fixation member 622. Fixation member 622 may be the same as or substantially similar to fixation members 122, 222, 322, 422, and/or 522 described above in reference to FIGS. 1-5B, except for the differences described herein. Fixation member 622 include a textured radially exterior surface 662. The textured radially exterior surface may include, for example, a surface having a surface roughness greater than a nontextured surface of fixation member 622. In some examples, textured radially exterior surface 662 may include an etched surface. For example, laser etching may be used to form recesses in surface 662. In some examples, textured radially exterior surface 662 may include coating. For example, a coating may include a binder and particles that define a rough surface, relative to an uncoated fixation member 622. In some examples, the roughness of textured radially exterior surface 662 may be selected to increase the surface area of the exterior surface of fixation member 622 and/or reduce shear between fixation member 622 and an overmolded distal member at exterior surface 662 in response to a push force and/or a pull force.

Figure 7B:
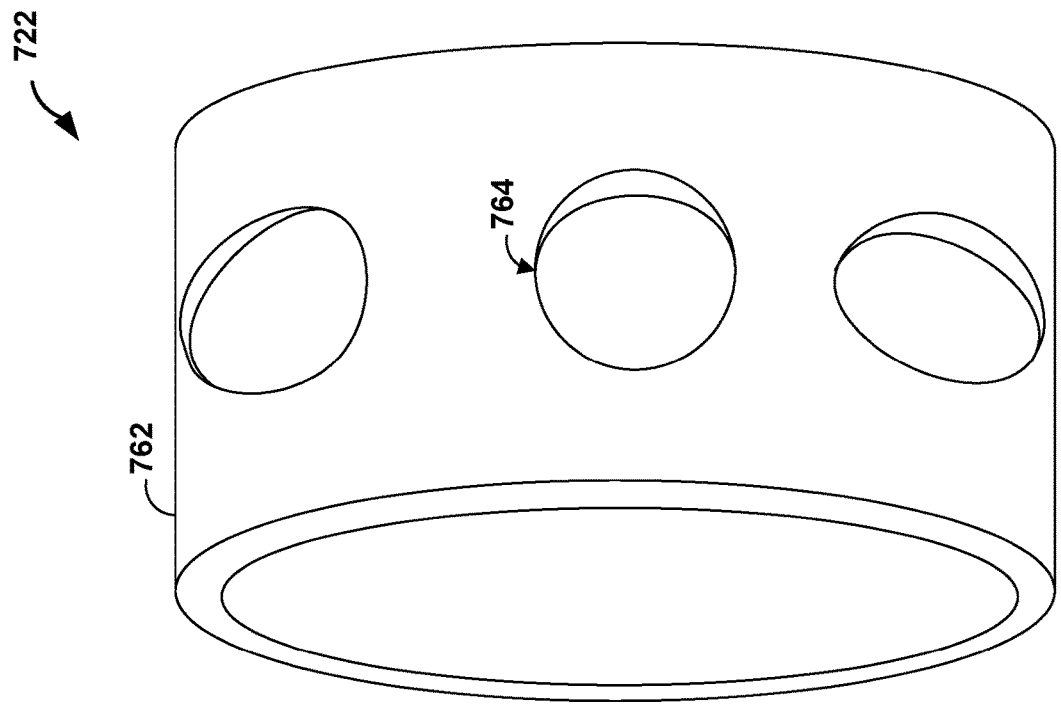
FIGS. 7A and 7B are conceptual diagrams illustrating a lateral cross-sectional view and a perspective view of an example fixation member.
Figure 7A:
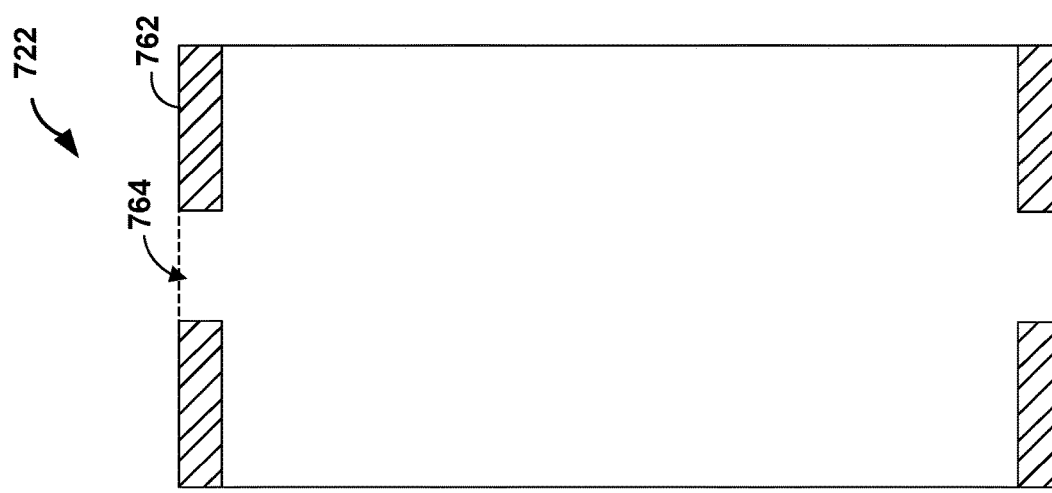

FIGS. 7A and 7B are conceptual diagrams illustrating a lateral cross-sectional view and a perspective view of an example fixation member 722. Fixation member 722 may be the same as or substantially similar to fixation members 122, 222, 322, 422, 522 and/or 622 described above in reference to FIGS. 1-6, except for the differences described herein. Fixation member 722 defines a plurality of through-holes 764 extending through fixation member 722 in the radial direction. Through-holes 764 may include any suitable shape, such as, for example, circular or rectilinear. Through-holes 764 may substantially straight sidewalls, e.g., normal to a tangent of exterior surface 762, or have tapered sidewalls. Tapered sidewall may improve material inflow during overmolding of a distal member, reduce formation of voids of the material of a distal member within the through-hole 764 during overmolding, or both. Through-holes 764 may be configured to enable material of an overmolded distal portion to extend from exterior surface 762 of fixation member 722 to an exterior surface of a distal portion of an elongate member (e.g., exterior surface 124). By extending to the exterior surface of the distal portion of the elongate member, the distal member may better engage the elongate member and/or reduce shear at the interface of the distal member and fixation member 722 relative to a fixation member without through-holes.

Figure 8B:
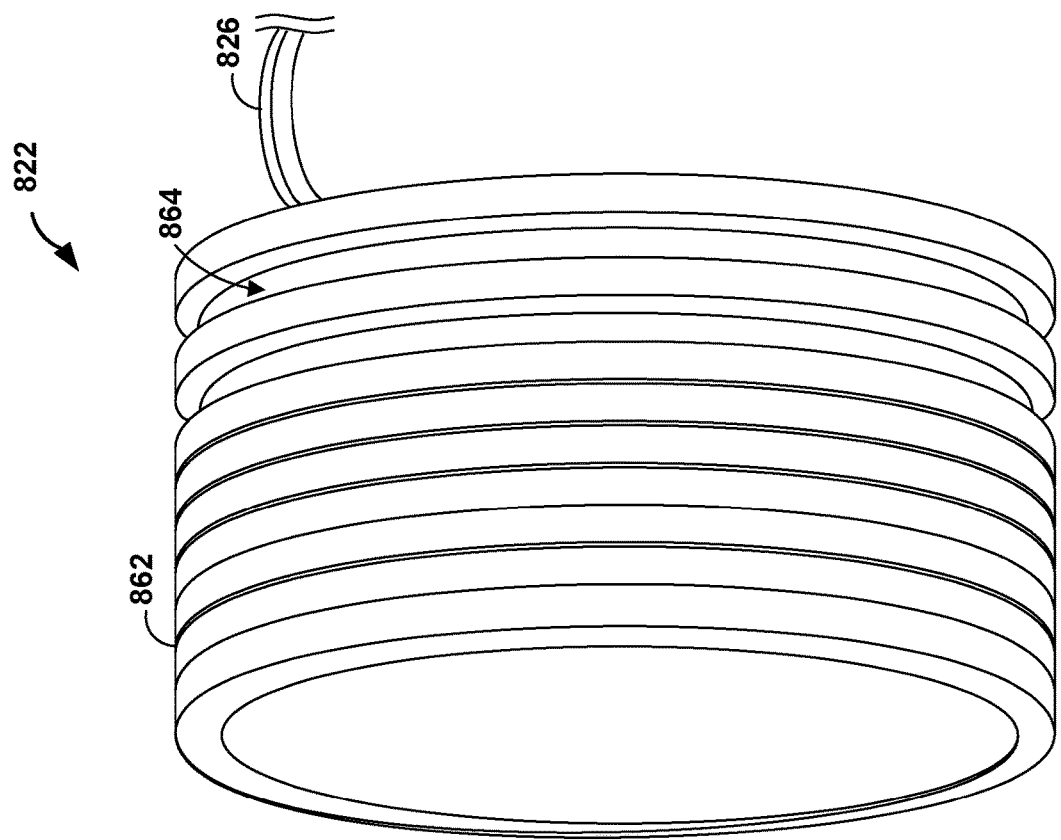
FIGS. 8A and 8B are conceptual diagrams illustrating a cross-sectional view and a perspective view of an example fixation member.
Figure 8A:
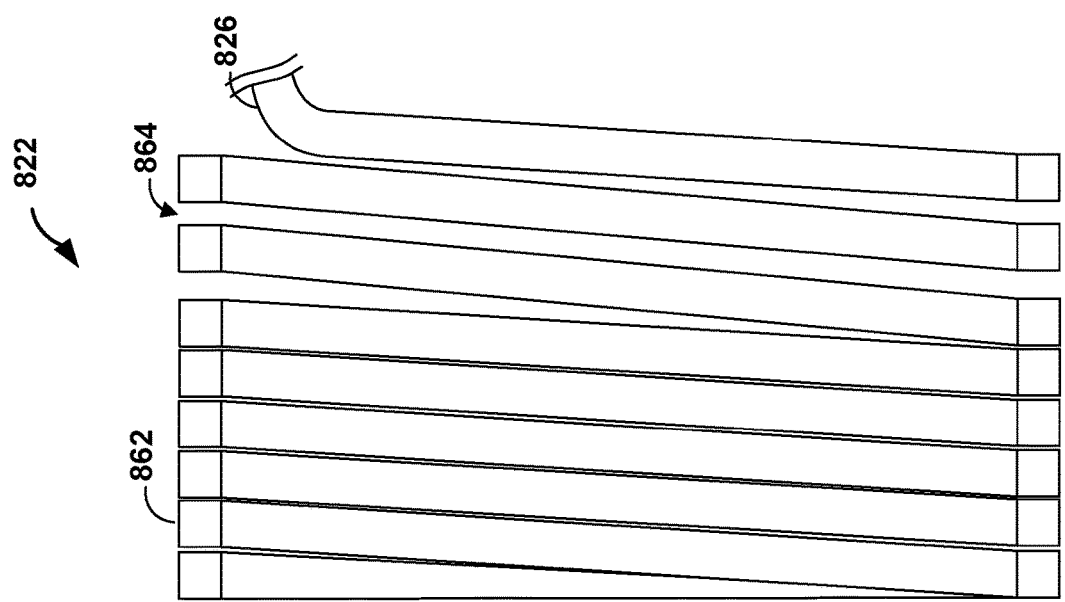

As discussed above in reference to FIG. 1, a pull wire and a fixation member may be integrally formed. For example, at least a portion of the fixation member may include a plurality of coil turns defined by a distal portion of the pull wire. FIGS. 8A and 8B are conceptual diagrams illustrating a cross-sectional view and a perspective view of an example fixation member 822. Fixation member 822 may be the same as or substantially similar to fixation members 122, 222, 322, 422, 522, 622, and/or 722 described above in reference to FIGS. 1-7B, except for the differences described herein. For example, fixation member 822 may include any suitable shape, such as a taper, a convex shape, a concave shape, or the like. Additionally, or alternatively, fixation member 822 may include one or more textured surfaces.

Fixation member 822 includes a plurality of coil turns 862. Coil turns 862 are sized to receive at least a distal portion of an elongate member and may extend circumferentially around the wall of the elongate member. As illustrated in FIGS. 8A and 8B, coil turns 862 are integrally formed with a distal portion of pull wire 826. For example, a distal portion of pull wire 826 may be wound around a distal portion of an elongate member to form coil turns 862. In other examples, coil turns 862 may be separately formed from pull wire 826 and, subsequently, fixed to pull wire 826, e.g., by welding or a fastener. Although illustrated of rectilinear, coil turns may include any suitable cross-section shape, such as, for example, circular or elliptical.

In some examples, adjacent coil turns 862 may define one or more gaps 864. Gaps 864 may be configured to enable material of an overmolded distal member to extend from exterior surface of coil turns 862 of fixation member 822 to an exterior surface of a distal portion of an elongate member (e.g., exterior surface 124). By extending to the exterior surface of the distal portion of the elongate member, the distal member may better engage the elongate member and/or reduce shear at the interface of the distal member and fixation member 822 relative to a fixation member without gaps.

Figure 9:
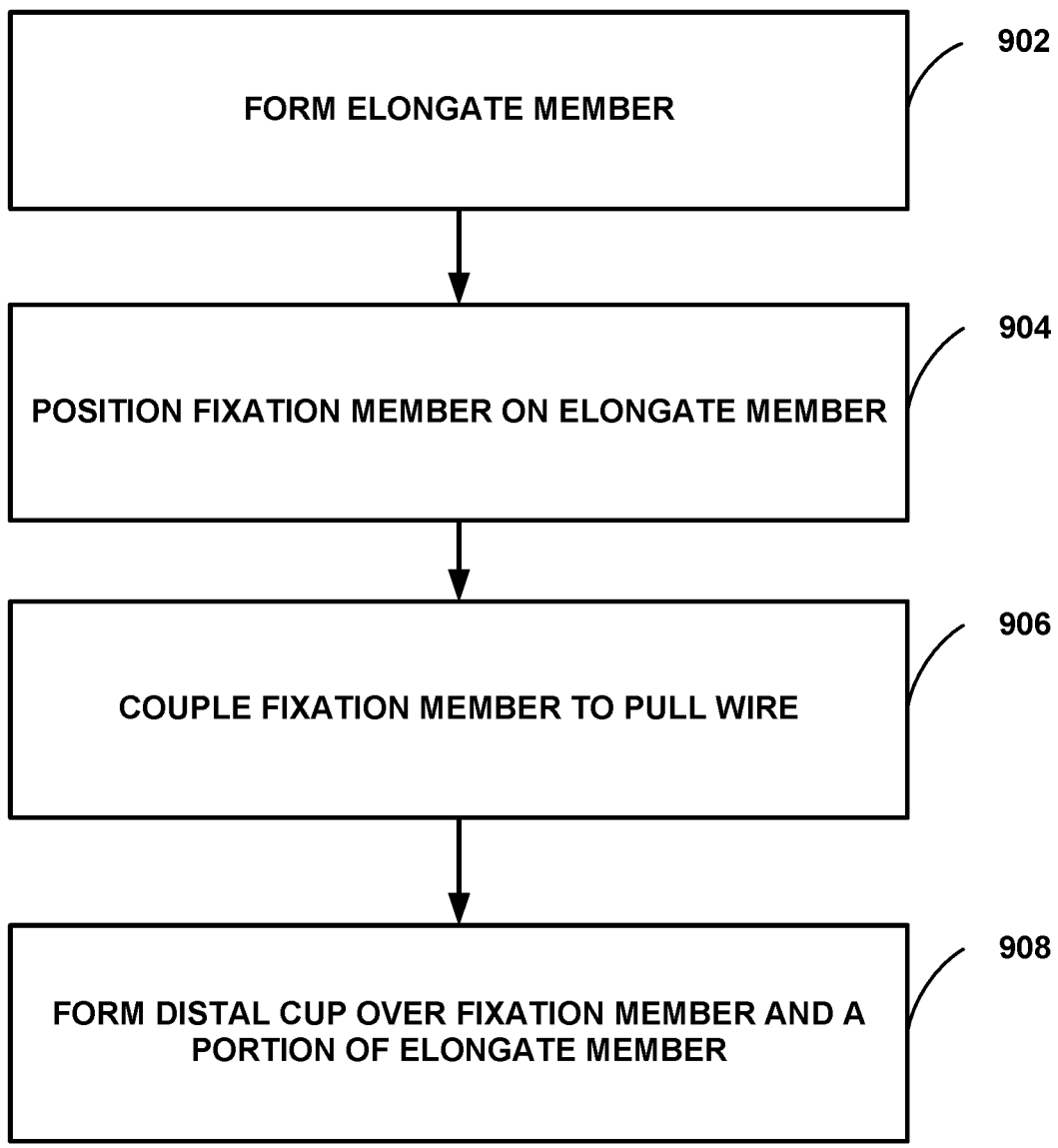
FIG. 9 is a flow diagram illustrating an example method of manufacturing a deflectable catheter.

The catheters described herein may be manufactured using any suitable technique. FIG. 9 is a flow diagram illustrating an example method of manufacturing a deflectable catheter. Although the technique illustrated in FIG. 9 is described in reference to catheter 200 illustrated in reference to FIGS. 2A and 2B, the technique may be used to manufacture other catheters or fixation members of catheters, such as catheter 100 or fixation members 322, 422, 522, 622, 722, and/or 822. Additionally, catheter 100 or fixation members 322, 422, 522, 622, 722, and/or 822 may be manufactured using other techniques.

The technique illustrated in FIG. 9 includes forming elongate member 202 (902). Forming elongate member 102 may include forming elongate member 102 extending from proximal end 206 to distal end 208, where elongate member 102 includes wall 240 defining a longitudinally extending lumen 242. In some examples, forming elongate member 202 may include, for example, positioning an inner layer 246 over a mandrel, positioning a sacrificial pull wire on inner layer 246, positioning a tubular member over the sacrificial pull wire and inner layer 246, positioning core layer 244 over the tubular member, and positioning outer layer 248 over the core layer 244. As discussed above, inner layer 246 may include any suitable polymer, such as, for example, polytetrafluoroethylene. As discussed above, outer layer 248 may include any suitable polymer, such as, for example, polyether block amide.

In some examples, positioning core layer 244 may include braiding two or more metal wires onto a mandrel. In some examples, forming core layer 244 may include forming core layer 244 directly over inner layer 246. In some examples, forming elongate core layer 244 may include abrading or coating an interior surface of an exterior surface of elongate core layer 244 prior to depositing inner layer 246 or outer layer 248 on a respective surface.

In some examples, rather than positioning core layer 244 on inner layer 246, the technique may include depositing on to interior surface 252 of core layer 244 a polymer to form inner layer 246. Any suitable deposition or coating method may be used to deposit inner layer 246. In some examples, inner layer 246 may be deposited onto a mandrel prior to forming elongate core layer 244 over inner layer 246. In some examples, pull wire 226 (or a sacrificial wire) may be positioned adjacent to interior surface 252 of core layer 244 prior to depositing inner layer 246 such that inner layer 246 may substantially encase pull wire 226.

In some examples, rather than positioning outer layer 248 over core layer 244, the technique may include depositing a polymer onto exterior surface 250 of core layer 244 to form outer layer 248. Any suitable deposition or coating method may be used to deposit outer layer 248. Outer layer 248 may at least partially flow into spaces between filars of core layer 244.

The technique illustrated in FIG. 9 includes positioning fixation member 222 on distal portion 216 of elongate member 202 (904). In some examples, positioning fixation member 222 on distal portion 216 of elongate member 202 may include sliding fixation member 222 over distal portion 216 to a selected region of distal portion 216. By sliding fixation member 222 on to distal portion 216, the technique may reduce manufacturing cost and/or reduce manufacturing complexity by eliminating steps that include, for example, at least one of removing material from distal portion 216 of elongate member 202 prior to positioning fixation member 222, overmolding fixation member 222 onto distal portion 216 of elongate member 202, or mechanically fastening fixation member 222 to distal portion 216 of elongate member 202.

In some examples, positioning fixation member 222 on distal portion 216 of elongate member 202 may include at least one of friction fitting or adhering fixation member 222 onto exterior surface 224 of wall 240. In examples in which fixation member 222 includes a polymeric material, positioning fixation member 222 on distal portion 216 of elongate member 202 may include heat-shrinking fixation member 222 onto exterior surface 224 of wall 240 or overmolding fixation member 222 onto exterior surface 224 of wall 240.

In examples in which fixation member 222 includes an annular band, positioning fixation member 222 may include positioning the annular band on exterior surface 224 of wall 240 on distal portion 216 of elongate member 202. Additionally, the technique may include forming the annular band. The annular band may be formed in any suitable shape, such as those describe above in reference to FIGS. 3-7B. In some examples, forming the annular band may include laser cutting the annular band from a hypotube, machining the annular band from a metal blank, casting the annular band, extruding a hard polymer band, injection molding the band, or additive manufacture of material for form the annular band. In some examples, forming the annular band may include etching the annular band or coating the annular band to form a textured radially exterior surface.

In examples in which fixation member 222 includes a distal portion 232 of pull wire 226, positioning fixation member 222 may include winding distal portion 232 of pull wire 226 to define a plurality of coil turns (e.g., coil turns 826). Winding distal portion 232 of pull wire 226 may include winding distal portion 232 to define a selected shape, such as a shape discussed above in reference to FIGS. 8A and 8B. In some examples, the technique also may include positioning the plurality of coil turns to extend circumferentially around wall 240 of distal portion 216 of elongate member 202. In some examples, positioning the plurality of coils may include positioning the plurality of coil turns to define a gap between at least two adjacent coil turns.

The technique illustrated in FIG. 9 includes coupling pull wire 226 to fixation member 222 (906). For example, in examples in which fixation member 222 includes an annular band or a separately formed plurality of coil turns, coupling pull wire 226 to fixation member 222 may include welding, adhering, or mechanically fastening pull wire 226 to fixation member 222. In examples in which fixation member 222 is integrally formed with pull wire 226, coupling pull wire 226 to fixation member 222 may include forming the plurality of coil turns.

The technique illustrated in FIG. 9 includes forming distal member 234 over at least a portion of fixation member 222 and a portion of distal portion 216 of elongate member 202 (908). For example, forming distal member 234 may include overmolding distal member 234 onto distal portion 216 of elongate member 202 to encase at least a portion of fixation member 222. In some examples, fixation member 222 may be overmolded to encase at least a portion of distal portion 232 of pull wire 226. In some examples, before or after overmolding fixation member 222, the technique may include knotting, looping, and/or welding a bulbous structure to distal portion 232 of pull wire 226.

Figure 10:
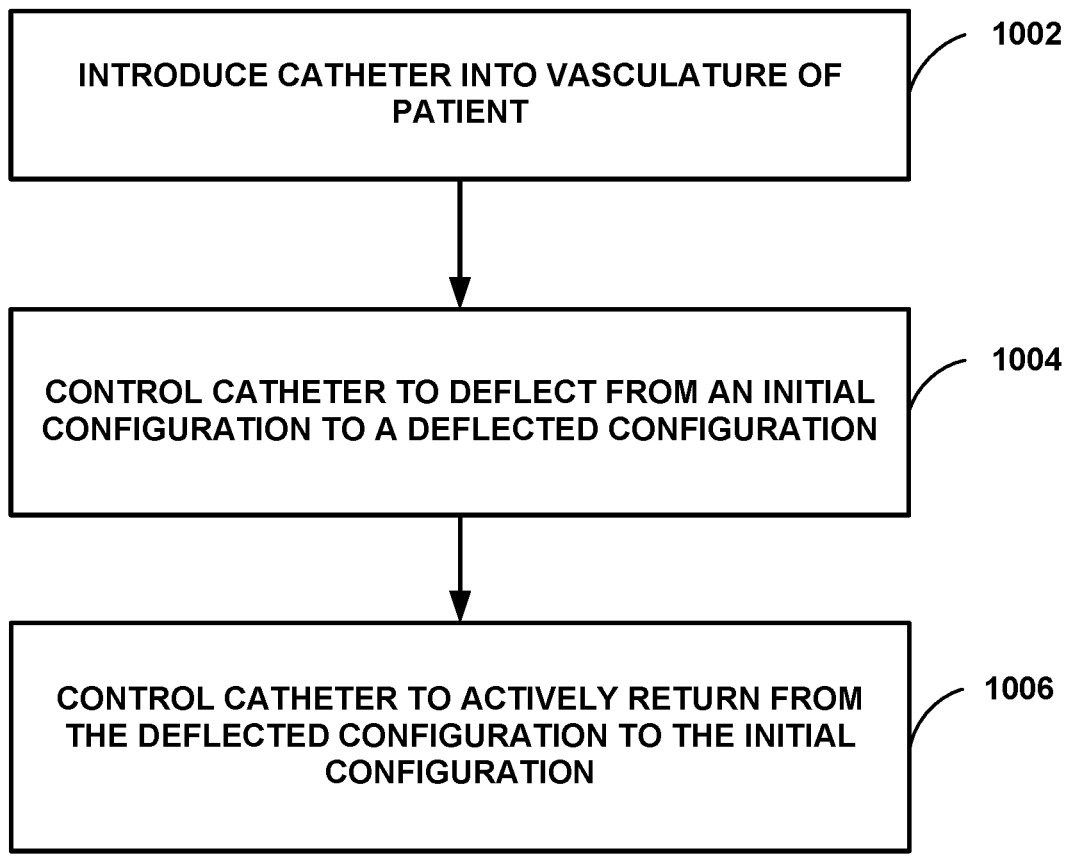
FIG. 10 is a flow diagram illustrating an example method of using a deflectable catheter.

The catheters described herein may be used to delivery an implantable medical device to a target site within a body of a patient. FIG. 10 is a flow diagram illustrating an example method of using a deflectable catheter. Although the technique illustrated in FIG. 10 is described in reference to catheter 100 illustrated in reference to FIG. 1, the technique may be used with other catheters, such as catheter 200 or catheters having a fixation member, such as fixation members 322, 422, 522, 622, 722, and/or 822. Additionally, catheters 100 or 200, or fixation members 322, 422, 522, 622, 722, and/or 822 may be used with other techniques.

The technique illustrated in FIG. 10 includes introducing distal portion 116 of elongate member 102 of catheter 100 into vasculature of a patient (1002). In some examples, introducing catheter 100 may include creating an incision in the femoral vein of the patient.

After introducing catheter 100, the technique may include navigating catheter 100 to a target location within the patient, such as renal arteries, a chamber of the heart, a location in the lung, a gastrointestinal location, or the like. In some examples, navigating may include using fluoroscopy to visualize a location of catheter 100 relative to an anatomy of the patient. Navigating catheter 100 includes controlling catheter 100, via pull wire 126 coupled to fixation member 122, to deflect at least distal portion 116 of elongate member 102 from an initial configuration to a deflected configuration (1004), and, optionally, controlling catheter 100, via pull wire 126 coupled to fixation member 122, to actively return from the deflected configuration to the initial configuration (1006). The technique also may include deploying an IMD from a distal member 134, e.g., delivery cup, of catheter 100 to the target location within the vasculature of the patient.

The following clauses illustrate example subject matter described herein.

Clause 1: A catheter comprising: an elongate member extending from a proximal end to a distal end, wherein the elongate member comprises a wall defining a longitudinally extending lumen; a fixation member disposed on an exterior surface of the wall of a distal portion of the elongate member; a pull wire extending axially through the wall of the elongate member from the proximal end of the elongate member to the fixation member, wherein the pull wire is coupled to the fixation member; and a distal member extending from the distal portion of the catheter to a distal end of the distal member, wherein the distal member encases at least a portion of the fixation member and the fixation member is shaped to engage the distal member, wherein the elongate member is configured to deflect from an initial configuration to a deflected configuration in response to a pull force applied to the pull wire.

Clause 2: The catheter of clause 1, wherein the fixation member comprises an annular band defining at least one of a radially outward extending exterior surface or a radially inward extending exterior surface.

Clause 3: The catheter of clause 1 or 2, wherein the fixation member comprises an annular band defining at least one of a convex shape or a concave shape.

Clause 4. The catheter of any one of clauses 1 through 3, wherein the fixation member comprises an annular band defining a textured radially exterior surface.

Clause 5: The catheter of any one of clauses 1 through 4, wherein the fixation member comprises an annular band defining a through-hole, and wherein a portion of the distal member extends through the through-hole to the exterior surface of the wall of the elongate member.

Clause 6. The catheter of 1, wherein the pull wire and the fixation member are integrally formed.

Clause 7: The catheter of clause 1 or 6, wherein the fixation member comprises a plurality of coil turns defined by a distal portion of the pull wire, wherein the plurality of coil turns extend circumferentially around the wall of the elongate member.

Clause 8: The catheter of clause 7, wherein the plurality of coil turns define at least one of a convex shape or a concave shape.

Clause 9: The catheter of clause 7 or 8, wherein the plurality of coil turns define at least one gap between at least a first coil turn and a second coil turn of the plurality of coil turns, and wherein the distal member extends through the at least one gap to the exterior surface of the wall of the elongate member.

Clause 10: The catheter of any one of clauses 1 through 9, wherein the fixation member is configured to engage the exterior surface of the wall of the elongate member by at least one of a friction fit, a compression fit, or an overmold and couple to a distal end of the pull wire.

Clause 11: The catheter of any one of clauses 1 through 10, wherein the elongate member is further configured to deflect from the deflected configuration to the initial configuration in response to a push force applied to the pull wire.

Clause 12: The catheter of any one of clauses 1 through 11, wherein the pull wire extends from the proximal end of the elongate member to the fixation member through at least a portion of the wall of the elongate member.

Clause 13: The catheter of any one of clauses 1 through 12, wherein the wall comprises: an elongate core layer defining an exterior surface and an interior surface defining the longitudinally extending lumen, wherein the elongate core layer comprises a coiled or braided metal wire; an inner layer disposed on the interior surface of the elongate core layer; and an outer layer disposed on the exterior surface of the elongate core layer, wherein the pull wire is disposed at least one of between the inner layer and the core layer or through the inner layer.

Clause 14: The catheter of any one of clauses 1 through 13, wherein a distal end of the pull wire comprises at least one of a bulbous structure, a loop, a knot, a weld bead, or a washer.

Clause 15: The catheter of any one of clauses 1 through 14, wherein the distal member comprises an overmolded polymer.

Clause 16: A catheter comprising: an elongate member extending from a proximal end to a distal end, wherein the elongate member comprises a wall defining a longitudinally extending lumen; a pull wire extending axially through the wall of the elongate member from the proximal end of the elongate member to the fixation member; and a fixation member disposed on an exterior surface of the wall of a distal portion of the elongate member, wherein the fixation member is coupled to the pull wire or integrally formed with the pull wire; a distal member extending from the distal portion of the catheter to a distal end of the distal member, wherein the distal member encases the fixation member, wherein the fixation member is configured to engage the distal member in response to a pull force applied to the pull wire to cause the elongate member to deflect from an initial configuration to a deflected configuration.

Clause 17: A method comprising: forming an elongate member extending from a proximal end to a distal end, wherein the elongate member comprises a wall defining a longitudinally extending lumen; positioning a fixation member on an exterior surface of the wall on a distal portion of the elongate member; coupling a pull wire to the fixation member, wherein the pull wire extends through the wall of the elongate member from the proximal end of the elongate member to the fixation member; and forming a distal member over at least a portion of the fixation member and a portion of the distal portion of the elongate member, wherein the distal member extends from the distal portion of the catheter to a distal end of the distal member, wherein the distal member encases at least a portion of the fixation member, wherein the fixation member is shaped to engage the distal member, and wherein the elongate member is configured to deflect from an initial configuration to a deflected configuration in response to a pull force applied to the pull wire.

Clause 18: The method of clause 17, wherein forming the elongate member comprises: positioning the pull wire adjacent to an exterior surface of an elongate core layer of the elongate member; and forming an outer layer on an exterior surface of the elongate core layer, wherein the pull wire extends through the outer layer from the proximal end of the elongate member to the fixation member.

Clause 19: The method of clause 17 or 18, wherein the fixation member comprises an annular band, wherein positioning the fixation member comprises positioning the annular band on the exterior surface of the wall on the distal portion of the elongate member.

Clause 20: The method of any one of clauses 17 through 19, wherein the annular band comprises at least one of radially outward extending exterior surface, a radially inward extending exterior surface, a convex shape, a concave shape, textured radially exterior surface, or defines a through-hole.

Clause 21: The method of any one of clauses 17 through 20, wherein the fixation member comprises a distal portion of the pull wire, wherein positioning the fixation member comprises: winding the distal portion of the pull wire to define a plurality of coil turns; and positioning the plurality of coil turns to extend circumferentially around the wall of the distal portion of the elongate member.

Clause 22: The method of any one of clauses 17 through 21, wherein coupling the pull wire to the fixation member comprises welding the distal end of the pull wire to the fixation member.

Clause 23: The method of any one of clauses 17 through 22, wherein coupling the pull wire to the fixation member comprises overmolding the distal member to onto at least a portion of the fixation member and a distal portion of the pull wire.

Clause 24: The method of any one of clauses 17 through 23, wherein the elongate member is configured to deflect from the deflected configuration to the initial configuration in response to a push force applied to the pull wire.

Clause 25: The method of claim 17, wherein the catheter comprises the catheter of any one of claims 1 through 15.

Various examples of the disclosure have been described. Any combination of the described systems, operations, or functions is contemplated. These and other examples are within the scope of the following claims.

What is claimed is:

1. A catheter comprising:
   an elongate member extending from a proximal end to a distal end, wherein the elongate member comprises a wall defining a longitudinally extending lumen;
   a fixation member;
   a pull wire extending axially through the wall from the proximal end of the elongate member to the fixation member, wherein the pull wire is coupled to the fixation member; and
   a distal member extending from the distal end of the elongate member to a distal end of the distal member, wherein the distal member is configured to receive a leadless cardiac pacing device and deploy the leadless cardiac pacing device within a heart of a patient,
   wherein the leadless cardiac pacing device comprises a pulse generator configured to deliver pacing therapy,
   wherein a distal end of the fixation member is spaced proximally from the distal end of the distal member,
   wherein the distal member encases at least a portion of the fixation member,
   wherein the fixation member comprises an annular band defining a through-hole, and wherein a portion of the distal member extends through the through-hole to an exterior surface of the wall of the elongate member, and
   wherein the elongate member is configured to deflect from an initial configuration to a deflected configuration in response to a pull force applied to the pull wire.

2. The catheter of claim 1, wherein the annular band defines at least one of a radially outward extending exterior surface or a radially inward extending exterior surface.

3. The catheter of claim 1, the annular band defines at least one of a convex shape or a concave shape.

4. The catheter of claim 1, the annular band defines a textured radially exterior surface.

5. The catheter of claim 1, wherein the pull wire and the fixation member are integrally formed.

6. The catheter of claim 1, wherein the fixation member comprises a plurality of coil turns defined by a distal portion of the pull wire, wherein the plurality of coil turns extend circumferentially around the wall of the elongate member.

7. The catheter of claim 6, wherein the plurality of coil turns define at least one of a convex shape or a concave shape.

8. The catheter of claim 6, wherein the plurality of coil turns define at least one gap between at least a first coil turn and a second coil turn of the plurality of coil turns.

9. The catheter of claim 1, wherein the fixation member is configured to:
engage an exterior surface of the wall of the elongate member by at least one of a friction fit, a compression fit, or an overmold; and
couple to a distal end of the pull wire.

10. The catheter of claim 1, wherein the elongate member is further configured to deflect from the deflected configuration to the initial configuration in response to a push force applied to the pull wire.

11. The catheter of claim 1, wherein the pull wire extends from the proximal end of the elongate member to the fixation member through at least a portion of the wall of the elongate member.

12. The catheter of claim 1, wherein the wall comprises:
an elongate core layer defining an exterior surface and an interior surface defining the longitudinally extending lumen, wherein the elongate core layer comprises a coiled or braided metal wire;
an inner layer disposed on the interior surface of the elongate core layer; and
an outer layer disposed on the exterior surface of the elongate core layer,
wherein the pull wire is disposed at least one of between the inner layer and the core layer or through the inner layer.

13. The catheter of claim 1, wherein a distal end of the pull wire comprises at least one of a bulbous structure, a loop, a knot, a weld bead, or a washer.

14. The catheter of claim 1, wherein the distal member comprises an overmolded polymer.

15. A catheter comprising:
an elongate member extending from a proximal end to a distal end, wherein the elongate member comprises a wall defining a longitudinally extending lumen;
a pull wire extending axially through the wall of the elongate member from the proximal end of the elongate member to a fixation member coupled to the pull wire or integrally formed with the pull wire,
wherein the fixation member comprises a plurality of coil turns defined by a distal portion of the pull wire,
wherein the plurality of coil turns extend circumferentially around the wall of the elongate member,
wherein the plurality of coil turns define at least one gap between at least a first coil turn and a second coil turn of the plurality of coil turns, and
wherein the distal member extends through the at least one gap to an exterior surface of the wall of the elongate member; and
a distal member extending from the distal end of the elongate member to a distal end of the distal member,
wherein the distal member is configured to receive a leadless cardiac pacing device and deploy the leadless cardiac pacing device within a heart of a patient,
wherein the distal member encases the fixation member, and
wherein the fixation member is configured to engage the distal member in response to a pull force applied to the pull wire to cause the elongate member to deflect from an initial configuration to a deflected configuration.

16. The catheter of claim 1, wherein the fixation member is shaped to engage the distal member.

17. The catheter of claim 1, wherein the fixation member is disposed on an exterior surface of the wall at a distal portion of the elongate member.

18. The catheter of claim 15, wherein the fixation member is disposed on an exterior surface of the wall at a distal portion of the elongate member.

19. A method comprising:
forming an elongate member extending from a proximal end to a distal end, wherein the elongate member comprises a wall defining a longitudinally extending lumen;
positioning a fixation member of the elongate member, wherein the fixation member comprises an annular band defining a through-hole;
coupling a pull wire to the fixation member, wherein the pull wire extends through the wall of the elongate member from the proximal end of the elongate member to the fixation member; and
forming a distal member over at least a portion of the fixation member and a portion of the distal portion of the elongate member and extending a portion of the distal member through the through-hole to an exterior surface of the wall of the elongate member, wherein the distal member extends from the distal end of the elongate member to a distal end of the distal member,
wherein the distal member is configured to receive a leadless cardiac pacing device and deploy the leadless cardiac pacing device within a heart of a patient,
wherein the leadless cardiac pacing device comprises a pulse generator configured to deliver pacing therapy,
wherein a distal end of the fixation member is spaced proximally from the distal end of the distal member,
wherein the distal member encases at least a portion of the fixation member, and
wherein the elongate member is configured to deflect from an initial configuration to a deflected configuration in response to a pull force applied to the pull wire.

20. The method of claim 19, wherein forming the elongate member comprises:
positioning the pull wire adjacent to an exterior surface of an elongate core layer of the elongate member; and
forming an outer layer on an exterior surface of the elongate core layer, wherein the pull wire extends through the outer layer from the proximal end of the elongate member to the fixation member.

21. The method of claim 19, wherein positioning the fixation member comprises positioning the annular band on an exterior surface of the wall on the distal portion of the elongate member.

22. The method of claim 21, wherein the annular band comprises at least one of radially outward extending exterior surface, a radially inward extending exterior surface, a convex shape, a concave shape, or a textured radially exterior surface.

23. The method of claim 19, wherein the fixation member comprises a distal portion of the pull wire.

24. The method of claim 19, wherein coupling the pull wire to the fixation member comprises welding the distal end of the pull wire to the fixation member.

25. The method of claim 19, wherein coupling the pull wire to the fixation member comprises overmolding the distal member to onto at least a portion of the fixation member and a distal portion of the pull wire.

26. The method of claim 19, wherein the elongate member is configured to deflect from the deflected configuration to the initial configuration in response to a push force applied to the pull wire.

27. The method of claim 17, wherein the fixation member is shaped to engage the distal member.

28. The method of claim 19, wherein positioning the fixation member comprises disposing the fixation member on an exterior surface of the wall at a distal portion of the elongate member.

* * * * *